(12) United States Patent
Lefkowitz et al.

(10) Patent No.: US 6,444,268 B2
(45) Date of Patent: Sep. 3, 2002

(54) FUNCTIONALIZATION OF SUBSTRATE SURFACES WITH SILANE MIXTURES

(75) Inventors: Steven M. Lefkowitz, Millbrae; Geraldine Fulcrand; Douglas J. Dellinger, both of Sunnyvale; Charles Z. Hotz, San Mateo, all of CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/897,340

(22) Filed: Jul. 2, 2001

Related U.S. Application Data

(62) Division of application No. 09/145,015, filed on Sep. 1, 1998, now Pat. No. 6,258,454.

(51) Int. Cl.[7] .................................................. B05D 1/36
(52) U.S. Cl. .................. 427/337; 427/407.2; 427/412.1
(58) Field of Search .............................. 427/337, 407.2, 427/412.1

(56) References Cited

U.S. PATENT DOCUMENTS

| 4,539,061 A | 9/1985 | Sagiv | |
| 5,137,765 A | 8/1992 | Farnsworth | 428/64 |
| 5,266,222 A | 11/1993 | Willis et al. | 252/49.006 |
| 5,474,796 A | 12/1995 | Brennan | 427/2.13 |
| 5,510,481 A | 4/1996 | Bednarski et al. | 536/120 |
| 5,624,711 A | 4/1997 | Sundberg et al. | 427/261 |
| 5,716,705 A | 2/1998 | Wirth et al. | 428/391 |
| 5,985,551 A | 11/1999 | Brennan | 435/6 |

FOREIGN PATENT DOCUMENTS

| WO | WO 96/06895 | 3/1996 |

OTHER PUBLICATIONS

Wasserman et al, Langmuir, 5(4), pp. 1074–87, 1989.*
Silver et al, J. Biomed. Mater. Res., 29(4), pp. 535–48, 1995.*
Tao et al. , "Preparation and Characterization of Mixed Monolayer with Controllable Composition," *Bull. Inst. Chem. Academia Sinica* 35:23–30. Mar. 1988.

* cited by examiner

Primary Examiner—Erma Cameron
(74) Attorney, Agent, or Firm—Gordon M. Stewart

(57) ABSTRACT

Low surface energy functionalized surfaces on solid supports are provided by treating a solid support having hydrophilic moieties on its surface with a derivatizing composition containing a mixture of silanes. A first silane provides the desired reduction in surface energy, while the second silane enables functionalization with molecular moieties of interest, such as small molecules, initial monomers to be used in the solid phase synthesis of oligomers, or intact oligomers. Molecular moieties of interest may be attached through cleavable sites. Derivatizing compositions for carrying out the surface functionalization process are provided as well.

13 Claims, 4 Drawing Sheets

U.S. 6,444,268 B2

FUNCTIONALIZATION OF SUBSTRATE SURFACES WITH SILANE MIXTURES

CROSS REFERENCE TO RELATED APPLICATION(S)

This is a divisional of application Ser. No. 09/145,015 filed on Sep. 1, 1998 now U.S. Pat. No. 6,258,454.

TECHNICAL FIELD

This invention relates generally to chemical functionalization of surfaces to modify the properties thereof. More particularly, the invention relates to functionalization of a substrate with a silane mixture to reduce surface energy and thus constrain droplets of liquid that are applied to the substrate surface. A primary use of the invention is in the field of solid phase chemical synthesis, particularly solid phase synthesis of oligomer arrays.

BACKGROUND

Chemically modified, "functionalized," solid surfaces are necessary in many laboratory procedures involved in chemistry and biotechnology. One important application is in solid phase chemical synthesis, wherein initial derivatization of a substrate surface enables synthesis of polymers such as oligonucleotides and peptides on the substrate itself. Support-bound oligomer arrays, particularly oligonucleotide arrays, may be used in screening studies for determination of binding affinity and in diagnostic applications, i.e., to detect the presence of a nucleic acid containing a specific, known oligonucleotide sequence. Modification of surfaces for use in chemical synthesis has been described, for example, in U.S. Pat. No. 5,624,711 to Sundberg et al., in U.S. Pat. No. 5,266,222 to Willis et al., in U.S. Pat. No. 5,137,765 to Farnsworth, and in numerous other patents and publications.

In modifying siliceous or metal oxide surfaces, one technique that has been used is derivatization with bifunctional silanes, i.e., silanes having a first functional group enabling covalent binding to the surface (often an Si-halogen or Si-alkoxy group, as in $-SiCl_3$ or $-Si(OCH_3)_3$, respectively) and a second functional group that can impart the desired chemical and/or physical modifications to the surface. A problem with this type of surface modification, however, is that incorporation of a desirable surface chemical functionality—provided by the second functional group—may result in a surface with undesirable physical properties. For example, there is currently a great deal of interest in synthesizing arrays of different oligonucleotides on siliceous surfaces, and a high density of array features is generally considered desirable. The various array features can be independently created by the planar separation of individual phosphoramidite coupling reactions as the oligonucleotides are synthesized; a simple way to achieve this separation is by spotting the phosphoramidite solutions onto the surface. Feature density is then determined by the spread of the solution droplet, which is in turn uniquely determined by both the volume of the droplet and the contact angle between the droplet and the surface. However, to covalently couple the first nucleotide phosphoramidite to the substrate surface requires hydroxyl moieties on the surface, which makes the surface wettable by the phosphoramidite solutions and thus creates droplet spread; for a given droplet volume, then, relatively large array features are provided, limiting feature density.

The aforementioned problem can be overcome using a variety of techniques to constrain the droplets as they are applied to the substrate surface. Permanent wells can be formed by micromachining the substrate, with the active surfaces subsequently modified, constraining the droplet by capillary action. Temporary wells can also be formed using either a pre-formed "stencil" or by applying a coating to the substrate and patterning the coating. These wells could constrain the droplet by either capillary action and/or by using a relatively unwettable coating. Alternatively, as described in U.S. Pat. No. 5,474,796 to Brennan, a pattern of two different surface-bound silanes can be formed by physically masking the surface, depositing the first silane, and then removing the mask and depositing the second silane. This procedure can be used to constrain a droplet by surrounding a reactive spot on the surface, formed by one of the two silanes, with a lower surface energy spot, formed by the other of the two silanes.

All of these procedures, however, require considerable processing and thus add substantially to the time and cost required to fabricate an array. Also, the existence of a pattern on the substrate requires that the array writing apparatus be aligned with the surface pattern, a non-trivial issue for small array features.

The present invention is directed to the aforementioned need in the art, and provides a way of functionalizing substrate surfaces to reduce surface energy and thus constrain droplets of liquid that are applied to the substrate surface, while avoiding the aforementioned problems and difficulties associated with the procedures of the prior art.

SUMMARY OF THE INVENTION

Accordingly, it is a primary object of the invention to address the aforementioned need in the art and provide a relatively simple, straightforward process for preparing a low surface energy functionalized surface on a substrate.

It is an additional object of the invention to provide such a process by coupling a mixture of silanes to hydrophilic moieties present on a substrate surface.

It is another object of the invention to provide a process for preparing support-bound cleavable ligands on a low surface energy substrate, wherein the ligands may be small molecules, oligonucleotides, oligopeptides, or the like.

It is another object of the invention to provide a derivatizing composition for preparing a low surface energy functionalized surface on a substrate.

It is still another object of the invention to provide such a derivatizing composition comprising a mixture of silanes.

It is yet another object of the invention to provide such a derivatizing composition comprising a first silane that upon binding to a substrate reduces the surface energy thereof, and a second silane that upon binding to a substrate provides a means for covalently binding molecular moieties to the substrate surface.

It is a further object of the invention to provide substrates having low surface energy functionalized surfaces.

Additional objects, advantages and novel features of the invention will be set forth in part in the description which follows, and in part will become apparent to those skilled in the art upon examination of the following, or may be learned by practice of the invention.

In one embodiment of the invention, then, a process is provided for preparing a low surface energy functionalized surface on a substrate, which comprises contacting a substrate having reactive hydrophilic moieties on its surface with a derivatizing composition comprising a first silane $R^1-Si(R^L R^x R^y)$ and a second silane $R^2-(L)_n-Si$ ($R^LR^xR^y$) under reaction conditions effective to couple the silanes to the substrate surface and provide —Si—$R^1$ groups and —Si—(L)$_n$—$R^2$ groups thereon. The $R^L$, which may be the same or different, are leaving groups, the $R^x$ and $R^y$, which may also be the same or different, are either leaving groups, like $R^L$, or are lower alkyl, $R^1$ is a chemically inert moiety that upon binding to the substrate surface lowers the surface energy thereof, n is 0 or 1, L is a linking group, and $R^2$ comprises either a functional group enabling covalent binding of a molecular moiety or a group that may be modified to provide such a functional group. The ratio of the silanes in the derivatizing composition determines the surface energy of the functionalized substrate and the density of molecular moieties that can ultimately be bound to the substrate surface.

In another embodiment, a process is provided for preparing support-bound cleavable ligands on a low surface energy substrate. The process involves contacting a substrate having reactive hydrophilic moieties on the surface thereof with a derivatizing composition comprising a first silane $R^1$—Si($R^LR^xR^y$) and a second silane $R^2$—(L)$_n$—Si($R^LR^xR^y$) as described above, under reaction conditions effective to couple the silanes to the substrate surface and provide —Si—$R^1$ groups and —Si—(L)$_n$—$R^2$ groups thereon. A ligand is then coupled to the surface at $R^2$, through a linking moiety containing a cleavable site. The ligand may be, for example, a small molecule, a first monomer in the solid phase synthesis of an oligomer, an intact oligomer, or the like.

In an additional embodiment, a derivatizing composition is provided for carrying out the aforementioned processes. The derivatizing composition comprises a mixture of silanes, including a first silane $R^1$—Si($R^LR^xR^y$) and a second silane $R^2$—(L)$_n$—Si($R^LR^xR^y$), wherein $R^1$, $R^2$, $R^L$, $R^x$, $R^y$ and n are as defined above.

Finally, the functionalized substrates provided using the presently disclosed and claimed processes and compositions represent a further embodiment of the invention. The substrates have surface-bound —Si—$R^1$ groups and —Si—(L)$_n$—$R^2$ groups, wherein the $R^1$ moieties reduce surface energy and the $R^2$ moieties comprise either functional groups enabling covalent attachment of a molecular moiety of interest or modifiable groups that can be converted to such functional groups.

DETAILED DESCRIPTION OF THE INVENTION

Overview and Definitions

Figure 1:
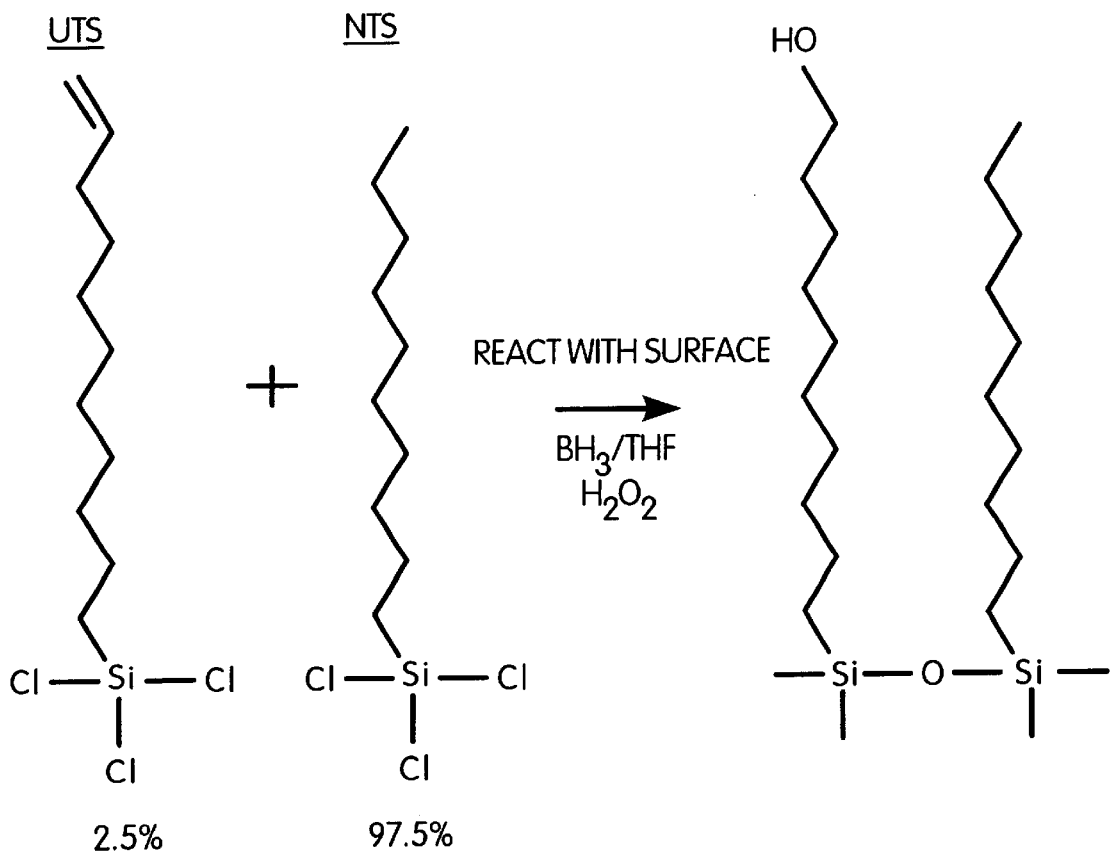
FIG. 1 schematically illustrates the functionalization of a substrate surface with a derivatizing composition comprising 97.5 wt. % n-decyltrichlorosilane ("NDS") and 2.5 wt. % undecenyltrichlorosilane ("UTS"), as described in Example 1.

Before describing the present invention in detail, it is to be understood that this invention is not limited to specific compositions, reagents, process steps, or equipment, as such may vary. It is also to be understood that the terminology used herein is for the purpose of describing particular embodiments only, and is not intended to be limiting.

It must be noted that, as used in this specification and the appended n claims, the singular forms "a," "an" and "the" include plural referents unless the context clearly dictates otherwise. Thus, reference to "a first silane having the structural formula $R^1$—Si($R^LR^xR^y$)" includes mixtures of silanes having the recited structure, while, similarly, a second silane having the structural formula $R^2$—(L)$_n$—Si($R^LR^xR^y$)" includes mixtures of such silanes, "a cleavable site" includes a multiplicity of cleavable sites, and the like.

In describing and claiming the present invention, the following terminology will be used in accordance with the definitions set out below.

The term "functionalization" as used herein relates to modification of a solid substrate to provide a plurality of functional groups on the substrate surface. By a "functionalized surface" as used herein is meant a substrate surface that has been modified so that a plurality of functional groups are present thereon.

The terms "reactive hydrophilic site" or "reactive hydrophilic group" refer to hydrophilic moieties that can be used as the starting point in a synthetic organic process. This is contrast to "inert" hydrophilic groups that could also be present on a substrate surface, e.g, hydrophilic sites associated with polyethylene glycol, a polyamide or the like.

The "surface energy" γ (measured in ergs/cm$^2$) of a liquid or solid substance pertains to the free energy of a molecule on the surface of the substance, which is necessarily higher than the free energy of a molecule contained in the in the interior of the substance; surface molecules have an energy roughly 25% above that of interior molecules. The term "surface tension" refers to the tensile force tending to draw surface molecules together, and although measured in different units (as the rate of increase of surface energy with area, in dynes/cm), is numerically equivalent to the corresponding surface energy. By modifying a substrate surface to "reduce" surface energy is meant lowering the surface energy below that of the unmodified surface.

The term "monomer" as used herein refers to a chemical entity that can be covalently linked to one or more other such entities to form an oligomer. Examples of "monomers" include nucleotides, amino acids, saccharides, peptoids, and the like. In general, the monomers used in conjunction with the present invention have first and second sites (e.g., C-termini and N-termini, or 5' and 3' sites) suitable for binding to other like monomers by means of standard chemical reactions (e.g., condensation, nucleophilic displacement of a leaving group, or the like), and a diverse element which distinguishes a particular monomer from a different monomer of the same type (e.g., an amino acid side chain, a nucleotide base, etc.). The initial substrate-bound monomer is generally used as a building-block in a multi-step synthesis procedure to form a complete ligand, such as in the synthesis of oligonucleotides, oligopeptides, and the like.

The term "oligomer" is used herein to indicate a chemical entity that contains a plurality of monomers. As used herein, the terms "oligomer" and "polymer" are used interchangeably, as it is generally, although not necessarily, smaller "polymers" that are prepared using the functionalized substrates of the invention, particularly in conjunction with combinatorial chemistry techniques. Examples of oligomers and polymers include polydeoxyribonucleotides, polyribonucleotides, other polynucleotides which are—or C-glycosides of a purine or pyrimidine base, polypeptides, polysaccharides, and other chemical entities that contain repeating units of like chemical structure. In the practice of the instant invention, oligomers will generally comprise about 2–50 monomers, preferably about 2–20, more preferably about 3–10 monomers.

The term "ligand" as used herein refers to a moiety that is capable of covalently or otherwise chemically binding a compound of interest. Typically, when the present substrates are used in solid phase synthesis, they are used so that "ligands" are synthesized thereon. These solid-supported ligands can then be used in screening or separation processes, or the like, to bind a component of interest in a sample. The term "ligand" in the context of the invention may or may not be an "oligomer" as defined above. However, the term "ligand" as used herein may also refer to a compound that is not synthesized on the novel functionalized substrate, but that is "pre-synthesized" or obtained commercially, and then attached to the substrate.

The term "sample" as used herein relates to a material or mixture of materials, typically, although not necessarily, in fluid form, containing one or more components of interest.

The terms "nucleoside" and "nucleotide" are intended to include those moieties which contain not only the known purine and pyrimidine bases, but also other heterocyclic bases that have been modified. Such modifications include methylated purines or pyrimidines, acylated purines or pyrimidines, or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

As used herein, the term "amino acid" is intended to include not only the L-, D- and nonchiral forms of naturally occurring amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine), but also modified amino acids, amino acid analogs, and other chemical compounds which can be incorporated in conventional oligopeptide synthesis, e.g., 4-nitrophenylalanine, isoglutamic acid, isoglutamine, ε-nicotinoyl-lysine, isonipecotic acid, tetrahydroisoquinoleic acid, α-aminoisobutyric acid, sarcosine, citrulline, cysteic acid, t-butylglycine, t-butylalanine, phenylglycine, cyclohexylalanine, β-alanine, 4-aminobutyric acid, and the like.

The terms "protection" and "deprotection" as used herein relate, respectively, to the addition and removal of chemical protecting groups using conventional materials and techniques within the skill of the art and/or described in the pertinent literature; for example, reference may be had to Greene et al., *Protective Groups in Organic Synthesis*, 2nd Ed., New York: John Wiley & Sons, 1991. Protecting groups prevent the site to which they are attached from participating in the chemical reaction to be carried out.

The term "alkyl" as used herein refers to a branched or unbranched saturated hydrocarbon group of 1 to 24 carbon atoms, such as methyl, ethyl, n-propyl, isopropyl, n-butyl, isobutyl, t-butyl, octyl, decyl, tetradecyl, hexadecyl, eicosyl, tetracosyl and the like, as well as cycloalkyl groups such as cyclopentyl, cyclohexyl and the like. The term "lower alkyl" intends an alkyl group of 1 to 6 carbon atoms, preferably 1 to 4 carbon atoms.

The term "alkoxy" as used herein refers to a substituent —O—R wherein R is alkyl as defined above. The term "lower alkoxy" refers to such a group wherein R is lower alkyl.

The term "alkylene" as used herein refers to a difunctional saturated branched or unbranched hydrocarbon chain containing from 1 to 24 carbon atoms, and includes, for example, methylene (—CH$_2$—), ethylene (—CH$_2$—CH$_2$—), propylene (—CH$_2$—CH$_2$—CH$_2$—), 2-methylpropylene (—CH$_2$—CH(CH$_3$)—CH$_2$—), hexylene (—(CH$_2$)$_6$—), and the like. "Lower alkylene" refers to an alkylene group of 1 to 6, more preferably 1 to 4, carbon atoms.

The terms "alkenyl" and "olefinic" as used herein refer to a branched or unbranched hydrocarbon group of 2 to 24 carbon atoms containing at least one carbon-carbon double bond, such as ethenyl, n-propenyl, isopropenyl, n-butenyl, isobutenyl, t-butenyl, octenyl, decenyl, tetradecenyl, hexadecenyl, eicosenyl, tetracosenyl and the like.

The terms "halogen" or "halo" are used in the conventional sense to refer to a chloro, bromo, fluoro or iodo substituent.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present, and, thus, the description includes structures wherein a non-hydrogen substituent is present and structures wherein a non-hydrogen substituent is not present.

Accordingly, the invention in a first embodiment is directed to a process for preparing a low surface energy functionalized surface on a substrate. The functionalized surface prepared using this process has functional groups enabling covalent binding of molecular moieties, such as in solid phase chemical synthesis or the like, but nevertheless has lowered surface energy so that wettability is reduced and liquid droplets applied to the substrate surface are constrained (i.e., do not spread to the extent that they would in the absence of the presently disclosed and claimed surface modification process).

The inventive process involves contacting the surface of a solid substrate with a derivatizing composition that contains a mixture of silanes, under reaction conditions effective to couple the silanes to the substrate surface via reactive hydrophilic moieties present on the substrate surface. The reactive hydrophilic moieties on the substrate surface are typically hydroxyl groups, carboxyl groups, thiol groups, and/or substituted or unsubstituted amino groups, although, preferably, the reactive hydrophilic moieties are hydroxyl groups. The substrate may comprise any material that has a plurality of reactive hydrophilic sites on its surface, or that can be treated or coated so as to have a plurality of such sites on its surface. Suitable materials include, but are not limited to, supports that are typically used for solid phase chemical synthesis, e.g., cross-linked polymeric materials (e.g., divinylbenzene styrene-based polymers), agarose (e.g., Sepharose®), dextran (e.g., Sephadex®), cellulosic polymers, polyacrylamides, silica, glass (particularly controlled pore glass, or "CPG"), ceramics, and the like. The supports may be obtained commercially and used as is, or they may be treated or coated prior to functionalization.

The derivatizing composition contains two types of silanes, a first silane that may be represented as $R^1$—Si($R^L R^x R^y$) and a second silane having the formula $R^2$—(L)$_n$—Si($R^L R^x R^y$). In these formulae, the $R^L$, which may be the same or different, are leaving groups, the $R^x$ and $R^y$, which may be the same or different, are either lower alkyl or leaving groups like $R^L$, $R^1$ is a chemically inert moiety that upon binding to the substrate surface lowers the surface energy thereof, n is 0 or 1, L is a linking group, and $R^2$ is a functional group enabling covalent binding of a molecular moiety or a group that may be modified to provide such a functional group. Reaction of the substrate surface with the derivatizing composition is carried out under reaction conditions effective to couple the silanes to the surface hydrophilic moieties and thereby provide —Si—$R^1$ groups and —Si—(L)$_n$—$R^2$ groups on the substrate surface.

More specifically, the $R^L$ moieties, which are leaving groups, are such that they enable binding of the silanes to the surface. Typically, the leaving groups are hydrolyzable so as to form a silanol linkage to surface hydroxyl groups. Examples of suitable leaving groups include, but are not limited to, halogen atoms, particularly chloro, and alkoxy moieties, particularly lower alkoxy moieties. The $R^x$ and $R^y$ are either lower alkyl, e.g., methyl, ethyl, isopropyl, n-propyl, t-butyl, or the like, or leaving groups as just described with respect to $R^L$. Thus, each type of silane will generally contain a trichlorosilyl functionality, a tri(lower) alkoxysilyl functionality such as trimethoxysilyl, mixed functionalities such as diisopropylchlorosilyl, dimethylchlorosilyl, ethyldichlorosilyl, methylethylchlorosilyl or the like.

The first silane is the derivatizing agent that reduces surface energy as desired, while the second silane provides the surface functionalization necessary for covalent attachment of an additional molecular moiety, e.g., a ligand, a monomer, an oligomer, etc. Thus, with respect to the first silane, coupling to the substrate yields surface —Si—$R^1$ groups as explained above, wherein $R^1$ is a chemically inert moiety that upon binding to the substrate surface lowers surface energy. By "chemically inert" is meant that $R^1$ will not be cleaved or modified when the functionalized substrate is used for its intended purpose, e.g., in solid phase chemical synthesis, hybridization assays, or the like. Typically, $R^1$ is an alkyl group, generally although not necessarily containing in the range of 2 to 24 carbon atoms, preferably in the range of 10 to 18 carbon atoms. $R^1$ may also be benzyl, either unsubstituted or substituted with 1 to 5, typically 1 to 3, halogen, preferably fluoro, atoms.

The second silane, upon coupling, provides surface —Si—(L)$_n$—$R^2$ groups. Of course, if the $R^x$ and $R^y$ are not leaving groups, the surface moieties provided will actually be "—SiR$^x$R$^y$—(L)$_n$—$R^2$" groups, which applicants intend to encompass by the more generic representation "—Si—(L)$_n$—$R^2$". $R^2$ comprises either a functional group that can bind directly to an additional molecular species of interest, or a modifiable group that can be converted to such a functional group under conditions that do not substantially affect any other chemical species that are present. That is, $R^2$ may be a functional group such as hydroxyl, carboxyl, amino, or the like, or it may be a modifiable group such an olefinic moiety, e.g., a terminal —CH=CH$_2$ group, which can readily be converted to a reactive hydroxyl group by boration and oxidation using procedures known in the art. L represents a linker and n is 0 or 1, such that a linker may or may not be present. If a linker is present, it will generally be a $C_1$–$C_{24}$ hydrocarbylene linking group. Normally, L is $C_1$–$C_{24}$ alkylene, preferably $C_{10}$–$C_{18}$ alkylene.

The density of $R^2$ groups on the substrate surface, following reaction with the derivatizing composition, is determined by the relative proportions of the first and second silanes in the derivatizing composition. That is, a higher proportion of the second silane in the derivatizing composition will provide a greater density of $R^2$ groups, while a higher proportion of the first silane will give rise to a lower density of $R^2$ groups. Optimally, the first silane represents in the range of approximately 0.5 wt. % to 50 wt. % of the derivatization composition, preferably in the range of approximately 1.0 wt. % to 10 wt. % of the composition, while the second silane correspondingly represents in the range of approximately 50 wt. % to 99.5 wt. % of the derivatization composition, preferably in the range of approximately 90 wt. % to 99 wt. % of the composition.

Functionalized substrates prepared using the aforementioned procedures are believed to be novel and are claimed as such herein. The surface of the functionalized substrates contain both —Si—$R^1$ and Si—(L)$_n$—$R^2$ groups, present at a predetermined ratio, with the ratio determining both surface energy and density of functional groups. These substrates may be used, for example, in any of a number of known chemical and biological procedures, such as in solid phase chemical synthesis, e.g., of oligonucleotides, oligopeptides, and oligosaccharides, in the preparation of combinatorial libraries, in chemical separation procedures, in screening processes, and the like. Such procedures are in current use and will thus be known to those skilled in the art and/or described in the pertinent literature and texts. For example, synthesis of polynucleotide libraries using now conventional phosphoramidite or phosphotriester chemistry is described by Beaucage et al. (1981) *Tetrahedron Lett.* 22:1859–62, and Itakura et al. (1975) *J. Biol. Chem.* 250:4592 (1975). Houghten (1985) *Proc. Natl. Acad. Sci. USA* 82:5131–5135), describes the preparation of a combinatorial library of peptides using a modification of the Merrifield method (Merrifield (1963) *J. Am. Chem. Soc.* 85:2149–2154; Tam et al., *The Peptides* (New York: Academic Press, 1975), at pp. 185–249); and *Oligonucleotide Synthesis*, M. J. Gait, Ed. (New York: IRL Press, 1990).

For example, synthesis of support-bound oligonucleotides is normally conducted by successive addition of protected nucleotides to a growing oligonucleotide chain, wherein the terminal 5' hydroxyl group is caused to react with a deoxyribonucleoside-3'-O-(N,N-diisopropylamino) phosphoramidite protected at the 5' position with dimethoxytrityl or the like, the 5' protecting group is removed after the coupling reaction, and the procedure is repeated with additional protected nucleotides until synthesis of the desired oligonucleotide is complete.

Additionally, and as will be appreciated by those skilled in the art, oligopeptide synthesis on a support—as may be carried out herein by virtue of the support-bound $R^2$ substituent—involves sequential addition of carboxyl-protected amino acids to a growing peptide chain, with each additional amino acid in the sequence similarly protected and coupled to the terminal amino acid of the oligopeptide under conditions suitable for forming an amide linkage. After oligopeptide synthesis is complete, acid is used to remove the remaining terminal protecting groups. The support-bound oligopeptides thus provided can then be used in any number of ways, e.g., in screening procedures involved in combinatorial processes, in chromatographic methods, and the like.

In an alternative embodiment, the method and reagents of the invention are used to provide oligomers bound to the support via a chemically cleavable site. That is, in this alternative process, following reaction of the substrate surface with the first and second silanes, a further reaction is conducted at $R^2$. This reaction involves reaction of $R^2$ with a linking group containing a cleavable site, such as an ester group, and the free terminus of the bound linking group is then used for solid phase synthesis. Conversion of $R^2$ to a different moiety may or may not be desired prior to attaching the linking group. For example, $R^2$ may be an alkylamino substituent, in which case the amino moiety serves as the reactive site for binding the linking group, or $R^2$ may be bromo, in which case it is desirable to convert $R^2$ to a primary or secondary amino substituent, and then carry out the reaction to the linking group. In this way, the bound ligand, monomer, oligomer, or the like may be cleaved from the solid support by treatment of the surface with an appropriate reagent.

Suitable cleavable sites include, but are not limited to, the following: base-cleavable sites such as esters, particularly succinates (cleavable by, for example, ammonia or trimethylamine), quaternary ammonium salts (cleavable by, for example, diisopropylamine) and urethanes (cleavable by aqueous sodium hydroxide); acid-cleavable sites such benzyl alcohol derivatives (cleavable using trifluoroacetic acid), teicoplanin aglycone (cleavable by trifluoroacetic acid followed by base), acetals and thioacetals (also cleavable by trifluoroacetic acid), thioethers (cleavable, for example, by HF or cresol) and sulfonyls (cleavable by trifluoromethane sulfonic acid, trifluoroacetic acid, thioanisole, or the like); nucleophile-cleavable sites such as phthalamide (cleavable with substituted hydrazines), esters (cleavable with, for example, aluminum trichloride) and Weinreb amide (cleavable with lithium aluminum hydride); and other types of chemically cleavable sites, including phosphorothioate (cleavable with silver or mercuric ions) and diisopropyl-dialkoxysilyl (cleavable with fluoride ion). Other cleavable sites will be apparent to those skilled in the art or are described in thge pertinent literature and texts (e.g., Brown (1997) *Contemporary Organic Synthesis* 4(3):216–237).

It is to be understood that while the invention has been described in conjunction with the preferred specific embodiments thereof, the foregoing description as well as the example that follows are intended to illustrate and not limit the scope of the invention. Other aspects, advantages and modifications within the scope of the invention will be apparent to those skilled in the art to which the invention pertains.

All patents and publications mentioned herein, both supra and infra, are hereby incorporated by reference.

EXAMPLE 1

Preparation of Functionalized Surfaces

This example describes functionalization of a glass substrate with a derivatizing composition comprising 97.5 wt. % n-decyltrichlorosilane ("NTS") as a first silane and 2.5 wt. % undecenyltrichlorosilane ("UTS") as a second silane, followed by boration and oxidation to convert the terminal olefinic moiety of the surface-bound UTS to a hydroxyl group. This procedure is shown schematically in FIG. 1. Evaluation of the functionalized surface is also described.

(a) Silylation:

Under moisture-free conditions, 14 ml NTS and 0.4 ml UTS were added to 800 ml of anhydrous toluene, and swirled to mix. Cleaned glass substrates were placed into a ca. 1 liter reactor equipped for inert gas purging, heating and stirring, and purging was conducted for 30 minutes. Moisture-free conditions were maintained, and the NTS/UTS solution was added to the reactor. The solution was heated to 100° C. for 4 hours, while stirring and continuing to maintain moisture-free conditions. The silane solution was removed from the reactor and replaced with anhydrous toluene. This step was repeated twice.

The substrates were then removed from the reactor and rinsed rigorously with an appropriate solvent. The bulk solvent was removed from the substrates by blowing with clean inert gas. The substrates were placed in a vacuum oven preheated to 150° C. and heated under vacuum for 1 hour. The substrates were removed and allowed to cool to ambient temperature.

(b) Boration and Oxidation:

The silylated substrates prepared in part (a) were placed in a ca. 1 liter reactor equipped for inert gas purging and stirring, and purging was conducted for 30 minutes. Under moisture-free conditions, 800 ml of 1.0 M borane-tetrahydrofuran complex was transferred to the reactor. The substrates were incubated while stirring, for two hours. Then, while maintaining moisture-free conditions, the boration solution was removed and replaced with 800 ml anhydrous tetrahydrofuran. The substrates were removed and rinsed rigorously with an appropriate solvent. Bulk solvent was removed by blowing with clean inert gas.

To a 1 liter vessel equipped for stirring, 800 ml of 0.1 N NaOH in 30% hydrogen peroxide (aqueous) was added. The oxidized substrates were immersed therein, and incubated, with stirring, for 10 minutes. The substrates were removed and rinsed rigorously with an appropriate solvent, then dried by blowing with clean inert gas.

The processes of steps (a) and (b) were repeated using different mole ratios of NTS and UTS, 100% UTS, and a mixture of glycidoxypropyl trimethoxysilane and hexaethylene glycol (GOPS-HEG). This hydroxyl silane-linker was prepared following the procedure of Maskos et al. (Maskos et al. (1992) *Nucleic Acids Res.* 20:1679) who demonstrated it to be useful for both oligonucleotide synthesis and hybridization.

EXAMPLE 2

Evaluation of Functionalized Surfaces

Figure 2:
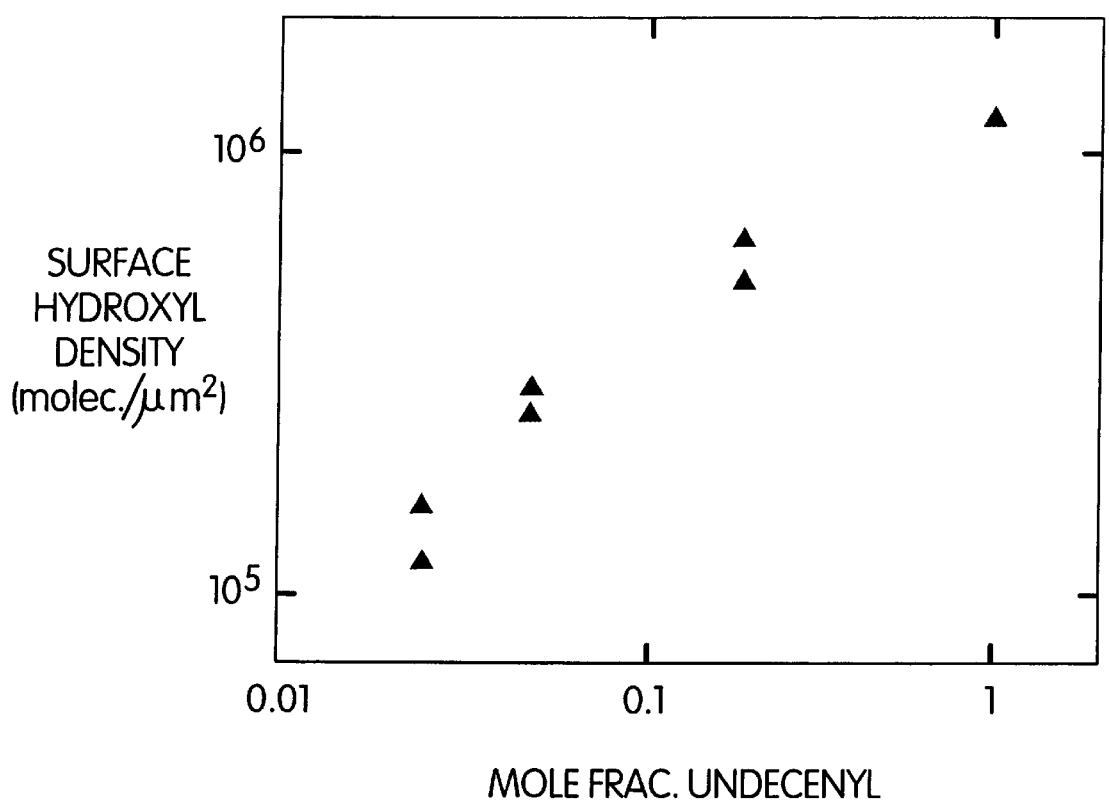
FIG. 2 is a graph showing the dependence of surface hydroxyl content on the mole ratio of UTS in the UTS/NTS derivatizing composition, evaluated as described in Example 2.
Figure 3:
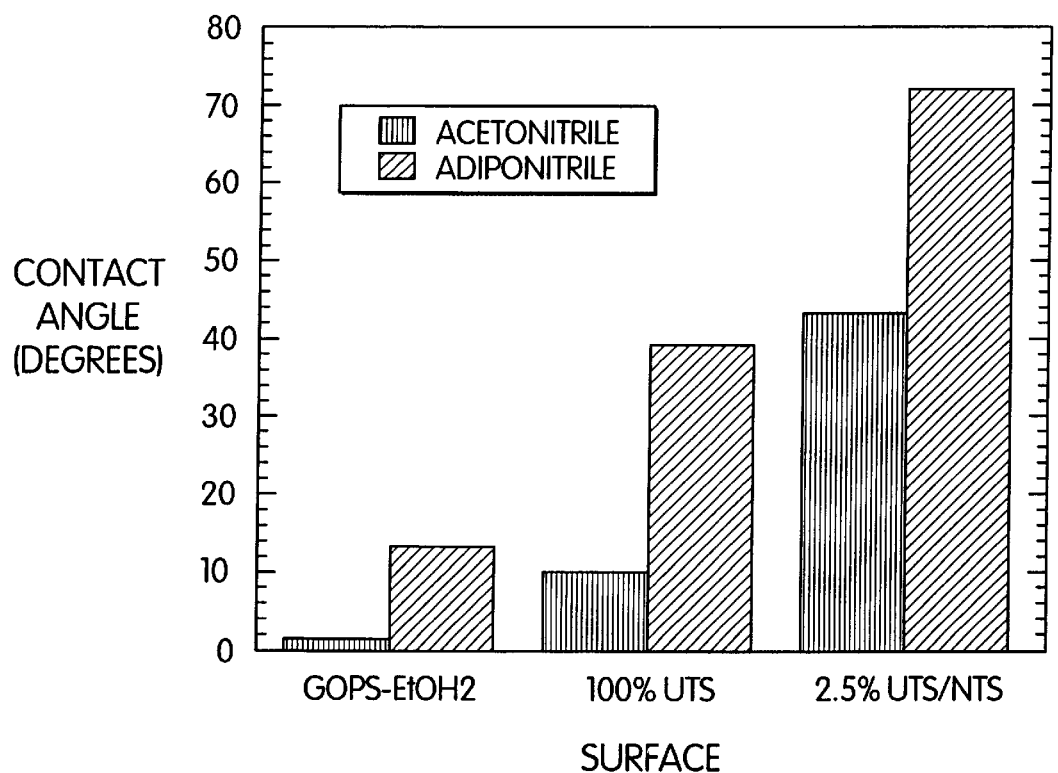
FIG. 3 illustrates, in graph form, the increase in contact angle for various derivatizing compositions, including a derivatizing composition of the invention, as described in Example 2.
Figure 4:
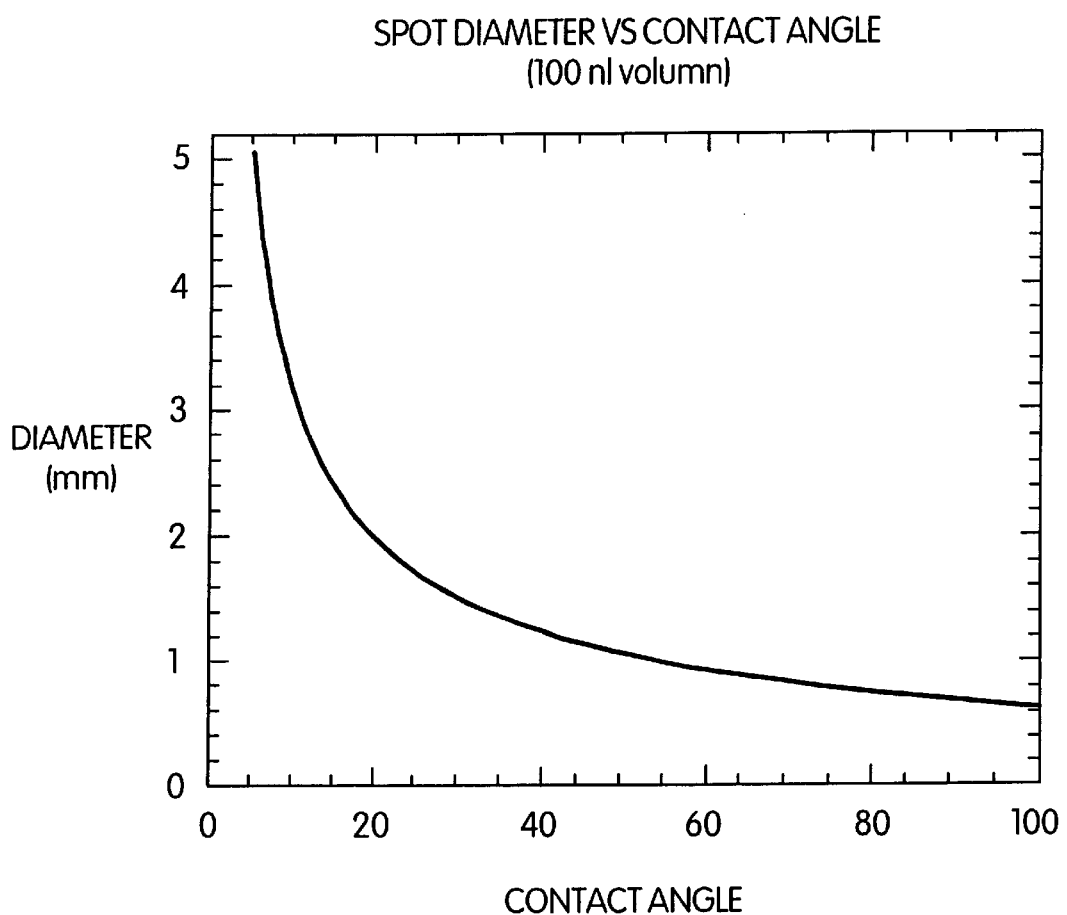
FIG. 4 is a graph showing the general relationship between spot diameter and contact angle, again, as described in Example 2.

Surface hydroxyl density (molecules/$\mu m^2$) of the functionalized surfaces prepared in Example 1 was evaluated spectrophotometrically, and FIG. 2 shows the dependence of surface hydroxyl content on the mole ratio of UTS in the UTS/NTS derivatizing composition. FIG. 3 shows the increase in contact angle for several UTS mole ratios and two solvents of interest, acetonitrile and adiponitrile, in comparison to a GOPS-ethanol mixture. Contact angles reported are static contact angle measurements as described in the literature (Chan, Chi-Ming, Polymer Surface Modification and Characterization, chapter 2 (New York: Hansa Publishers, 1993). Measurements were performed on 25 $\mu l$ aliquots of the appropriate solvent using an FTA200 instrument (First Ten Angstroms, South San Francisco, Calif.). FIG. 4 shows the general relationship between the spot diameter and contact angle. For 100 nl drops, the following spot diameters were observed for the GOPS-ethanol mixture and the 2.5% UTS/NTS derivatizing composition:

|  | GOPS-ethanol | 2.5% UTS/NTS |
| --- | --- | --- |
| acetonitrile | >5 mm | 1.4 mm |
| adiponitrile | 2.7 mm | 0.9 mm |

Thus, the derivatizing composition of the invention significantly reduces spot diameter for a droplet of a given volume.

What is claimed is:

1. A process for synthesizing an oligomer array on a substrate surface, comprising:

(a) functionalizing a substrate surface by contacting a substrate having reactive hydrophilic moieties on the surface thereof with a derivatizing composition comprising a first silane $R^1$—$Si(R^L R^x R^y)$ and a second silane $R^2$—$(L)_n$—$Si(R^L R^x R^y)$ under reaction conditions effective to couple the silanes to the substrate surface and provide —Si—$R^1$ groups and —Si—$(L)_n$—$R^2$ groups thereon, wherein the $R^L$, moieties, which may be the same or different, are groups which leave the silanes during the coupling, the $R^x$ and $R^y$ are independently lower alkyl or leaving groups, $R_1$ is a chemically inert moiety that upon binding to the substrate surface lowers the surface energy thereof, n is 0 or 1, L is a linking group, and $R^2$ is a functional group enabling covalent binding of a molecular moiety or a modifiable group that is capable of being converted to such a functional group; and (b) synthesizing a plurality of substrate-bound oligomers at each $R^2$ by sequentially coupling monomers thereto, wherein array features are created by the separation of individual coupling reactions as the oligomers are synthesized so as to form an oligomer array on the functionalized surface provided in (a);

wherein the substrate comprises a polymeric material, silica, glass, or ceramic.

2. The process of claim 1, wherein the monomers are amino acids and the oligomers are oligopeptides.

3. The process of claim 1, wherein the monomers are nucleotides and the oligomers are oligonucleotides.

4. The process of claim 1, wherein the monomers are protected and a deprotection step is carried out after each sequential coupling.

5. The process of claim 1, wherein prior to (b) a linking group is coupled to each $R^2$, and the monomers are sequentially coupled to a free terminus of the linking group.

6. The process of claim 5, wherein the linking group contains a site capable of being cleaved.

7. The process of claim 6, wherein the cleavable site is chemically cleavable.

8. A process for preparing an oligomer array, comprising:

(a) functionalizing a substrate surface by contacting a substrate having reactive hydrophilic moieties on the surface thereof with a derivatizing composition comprising a first silane $R^1$—$Si(R^L R^x R^y)$ and a second silane $R^2$—$(L)_n$—$Si(R^L R^x R^y)$ under reaction conditions effective to couple the silanes to the substrate surface and provide —Si—$R^1$ groups and —Si—$(L)_n$—$R^2$ groups thereon, wherein the $R^L$, moieties, which may be the same or different, are groups which leave the silanes during the coupling, the $R^x$ and $R^y$ are independently lower alkyl or leaving groups, $R^1$ is a chemically inert moiety that upon binding to the substrate surface lowers the surface energy thereof, n is 0 or 1, L is a linking group, and $R^2$ is a functional group enabling covalent binding of a molecular moiety or a modifiable group that is capable of being converted to such a functional group; and (b) binding a plurality of oligomers to the functionalized substrate by coupling an oligomer to each $R^2$;

wherein the substrate comprises a polymeric material, silica, glass, or ceramic.

9. A process according to claim 1 wherein the substrate comprises agarose, dextran, cellulosic polymers, or polyacrylamides.

10. A process according to claim 1 wherein the substrate comprises silica or glass.

11. A process according to claim 8 wherein the substrate comprises silica or glass.

12. A process for synthesizing an oligomer array on a substrate surface, comprising:

(a) functionalizing a substrate surface by contacting a substrate having reactive hydrophilic moieties on the surface thereof with a derivatizing composition comprising a first silane $R^1$—$Si(R^L R^x R^y)$ and a second silane $R^2$—$(L)_n$—$Si(R^L R^x R^y)$ under reaction conditions effective to couple the silanes to the substrate surface and provide —Si—$R^1$ groups and —Si—$(L)_n$—$R^2$ groups thereon, wherein the $R^L$, moieties, which may be the same or different, are groups which leave the silanes during the coupling, the $R^x$ and $R^y$ are independently lower alkyl or leaving groups, $R^1$ is a chemically inert moiety that upon binding to the substrate space lowers the surface energy thereof, n is 0 or 1, L is a linking group, and $R^2$ is a functional group enabling covalent binding of a molecular moiety or a modifiable group that is capable of being convened to such a functional group; and (b) synthesizing a plurality of substrate-bound oligomers at each $R^2$ by sequentially coupling monomers thereto, wherein array features are created by the separation of individual coupling reactions as the oligomers are synthesized so as to form an oligomer array on the functionalized surface provided in (a);

wherein the substrate has reactive hydrophilic moieities selected from any one or more of hydroxyl groups, carboxyl groups, thiol groups, and substituted or unsubstituted amino groups.

13. A process for preparing an oligomer array, comprising:

(a) functionalizing a substrate surface by contacting a substrate having reactive hydropbilic moieties on the surface thereof with a derivatizing composition comprising a first silane $R^1$—$Si(R^L R^x R^y)$ and a second silane $R^2$—$(L)_n$—$Si(R^L R^x R^y)$ under reaction conditions effective to couple the silanes to the substrate surface and provide —Si—$R^1$ groups and —Si—$(L)_n$—$R^2$ groups thereon, wherein the $R^L$, moieties, which may be the same or different, are groups which leave the silanes during the coupling, the $R^x$ and $R^y$ are independently lower alkyl or leaving groups, $R^1$ is a chemically inert moiety that upon binding to the substrate surface lowers the surface energy thereof, n is 0 or 1, L is a linking group, and $R^2$ is a functional group enabling covalent binding of a molecular moiety or a modifiable group that is capable of being converted to such a functional group; and (b) binding a plurality of oligomers to the functionalized substrate by coupling an oligomer to each $R^2$;

wherein the substrate has reactive hydrophilic moieities selected from any one or more of hydroxyl groups, carboxyl groups, thiol groups, and substituted or unsubstitited amino groups.

* * * * *